United States Patent [19]

Kubota et al.

[11] Patent Number: 5,090,995
[45] Date of Patent: Feb. 25, 1992

[54] AQUEOUS BIOCIDE COMPOSITION STABILIZED BY PHTHALIC ACID ESTERS

[75] Inventors: Yutaka Kubota; Seiichi Shimono; Tetsuo Yanami, all of Yokohama; Tetsuji Iwasaki; Kazuhiko Kurita, both of Wakayama, all of Japan

[73] Assignees: Mitsui Toatsu Chemicals, Inc.; Kao Corporation, both of Tokyo, Japan

[21] Appl. No.: 206,476

[22] Filed: Jun. 13, 1988

[30] Foreign Application Priority Data

Jun. 24, 1987 [JP] Japan ................. 62-157000

[51] Int. Cl.$^5$ ............. A01N 37/10; A01N 31/14
[52] U.S. Cl. ......................... 71/114; 71/100; 71/118; 71/121; 71/DIG. 1; 514/95; 514/99; 514/115; 514/436; 514/549; 514/721; 514/726; 568/609
[58] Field of Search ............. 568/609; 71/DIG. 1; 514/721

[56] References Cited

U.S. PATENT DOCUMENTS

| | | | |
|---|---|---|---|
| 3,898,075 | 8/1975 | Freund et al. | 71/111 |
| 4,071,617 | 1/1978 | Graves et al. | 424/78 |
| 4,460,406 | 7/1984 | Valange | 71/100 |
| 4,560,724 | 12/1985 | Brabetz et al. | 524/734 |
| 4,666,925 | 5/1987 | Sun | 514/721 |
| 4,812,483 | 3/1989 | Whittle | 514/721 |

FOREIGN PATENT DOCUMENTS

| | | |
|---|---|---|
| 0117999 | 9/1984 | European Pat. Off. . |
| 0173964 | 3/1986 | European Pat. Off. . |
| 0226815 | 7/1987 | European Pat. Off. . |
| 2448293 | 9/1980 | France . |
| 62-126101 | 6/1987 | Japan . |

OTHER PUBLICATIONS

Mitsui Toatsu Chemicals, Inc., *Insecticidal and Acaricidal Compositions*, Jpn. Kokai Tokkyo Koho Jp. 58, 49, 303 [83 49,303], 3/23/83.

Primary Examiner—Glennon H. Hollrah
Assistant Examiner—M. Clardy
Attorney, Agent, or Firm—Flynn, Thiel, Boutell & Tanis

[57] ABSTRACT

Disclosed is an agricultural chemical composition in the form of an aqueous suspension, which comprises fine particles of a water-insoluble physiologically active substance having a melting point of 15° to 70° C., which are stably dispersed in water by a water-soluble or water-dispersible polymer comprising at least one monomer selected from the group consisting of unsaturated carboxylic acids and derivatives thereof as the indispensable component, as a dispersant, and a phthalic acid ester as an agent for preventing precipitation of crystals.

In this agricultural chemical composition, the phthalic acid ester bleeds on the surface of the physiologically active substance to modify the surface, and the storage stability of the composition in the form of a suspension is highly improved.

12 Claims, No Drawings

AQUEOUS BIOCIDE COMPOSITION STABILIZED BY PHTHALIC ACID ESTERS

BACKGROUND OF THE INVENTION

(1) Field of the Invention

The invention relates to an aqueous biocide composition, improved in stability of suspension, useful especially in the agricultural field. More in particular, the invention relates to a composition in the form of an aqueous suspension in which a water-insoluble physiologically active substance having a melting point of 15° to 70° C. is stably dispersed so that precipitation of crystals is not caused during the storage.

(2) Description of the Prior Art

Water-insoluble physiologically active substances as agricultural chemicals have been heretofore used in the form of an emulsifiable concentrate or wettable powder, but recently, they are often used in the form of a suspension concentrate, flowable, obtained by dispersing fine particles of water-insoluble agricultural chemicals, for example, water-insoluble biocides, by using an appropriate dispersant. As the dispersant, there are proposed various anionic and non-ionic surface active agents and water-soluble polymeric surface active agents, and suspension concentrate which are stable even under severe storage conditions are provided.

However, in the case where a water-insoluble physiologically active substance having a melting point of 15° to 70° C. is used, if the suspension concentrate is stored under conditions where the temperature changes violently, development of crystals is caused in emulsified particles and therefore, such troubles as destruction of emulsified particles and precipitation of crystals take place.

SUMMARY OF THE INVENTION

As the means for stabilizing emulsions (suspensions), we made investigations on (1) a method in which a hydrophilic protective colloid is reinforced by forming an ion complex, (2) a method in which a hydrophilic colloid is formed by a hydrophobic-hydrophobic mutual action, and (3) a method in which surface modification is effected by the bleeding effect of a substance slightly different from the active substance in the solubility parameter. As the result, it was found that if a phthalic acid ester is used together with a specific dispersant in the method (3), there can be obtained a stable flowable suspension in which destruction of the emulsion or precipitation of crystals is not caused even during the storage under such severe conditions as those of the high temperature (50° C.)/low temperature (−10° C.) storage cycle test. We have now completed the present invention based on this finding.

The invention provides an aqueous biocide composition which comprises a water-insoluble, physiologically active substance in the form of fine particles having a melting point of 15° to 70° C., a water-soluble or water-dispersible polymer comprising one or more indispensable monomer units selected from the group consisting of an unsaturated carboxylic acid or its derivative and a phthalate, being in an aqueous dispersion of said particles. The composition comprises a biocidally effective amount of a biocide, or the physiologically active substance, the polymer in an effective amount for the dispersant, the phthalate in an effective amount of the precipitation-preventing agent and the balance, for example 10 to 90 wt. %, of water.

It is preferable that the composition comprises 10 to 60 wt. % of the physiologically active substance, 0.001 to 10 wt. % of the polymer, 0.01 to 30 wt. % of the phthalate and the balance of water and moreover comprises 10 to 60 wt. % of the physiologically active substance, 0.01 to 10 wt. % of the polymer, 0.1 to 30 wt. % of the phthalate and the balance of water.

The physiologically active substance is preferably selected from insecticides, fungicides, herbicides and acaricides. The unsaturated carboxylic acid or its derivative is preferably selected from acrylic acid, methacrylic acid, maleic acid, itaconic acid, an alkyl ester of the acid, an alkali metal salt of the acid, an ammonium salt of the acid and an organic amine salt of the acid. The polymer may be a copolymer with vinyl acetate, isobutylene, di-isobutylene, an alkylene ether or styrene. The phthalate is preferred to be a monoester or di-ester of phthalic acid and an alcohol having 4 to 22 carbon atoms.

The composition may further comprise up to 20 wt. % of a nonionic or anionic surfactant.

It is preferable from the practical point of view that the composition comprises 10 to 60 wt. % of a biocide, 0.01 to 10 wt. % of the polymer, 0.1 to 30 wt. % of the phthalate, up to 20 wt. % of the surfactant and 10 to 90 wt. % of water.

The composition advantageously improves the biocidal effect especially in the agricultural field.

DETAILED DESCRIPTION OF THE INVENTION

More specifically, in accordance with the present invention, there is provided an agricultural chemical composition in the form of an aqueous suspension, which comprises fine particles of a water-insoluble physiologically active substance having a melting point of 15° to 70° C., which are stably dispersed in water by a water-soluble or water-dispersible polymer comprising at least one monomer selected from the group consisting of unsaturated carboxylic acids and derivatives thereof as the indispensable component, as a dispersant, and a phthalic acid ester as an agent for preventing precipitation of crystals.

The phthalic acid ester used in the present invention is an esterification product of phthalic acid and an alcohol. As the alcohol forming an ester with phthalic acid, linear or branched alcohols having 4 to 22 carbon atoms are preferred, and alcohols having 10 to 18 carbon atoms are especially preferred. A monoester or diester can be used as the phthalic acid ester, and a diester is preferable.

The content of the phthalic acid ester in the agricultural chemical composition of the present invention is such that the weight ratio to the physiologically active substance is from 0.01 to 1, preferably from 0.05 to 0.8, especially preferably from 0.1 to 0.5.

The dispersant used in the present invention, that is, the water-soluble or water-dispersible polymer comprising at least one monomer selected from the group consisting of unsaturated carboxylic acids and derivatives thereof as the indispensable component will now be described in detail.

As the monomer to be used for the production of the polymer, there can be mentioned unsaturated monocarboxylic acids such as acrylic acid and methacrylic acid, unsaturated dicarboxylic acids such as maleic acid, and derivatives of these acids such as alkyl esters (for example, methyl esters), alkali metal salts (for example, sodium salts), ammonium salts, organic amine salts (for example, triethanolamine salts) of these acids, and mixtures thereof. In addition to the above-mentioned monomers, copolymerizable monomers such as vinyl acetate, isobutylene, diisobutylene and styrene can be used as the comonomer component.

Polymerization of the monomers can be accomplished according to known procedures. The proportion of the monomer components and the polymerization degree of the polymer are not particularly critical, but it is indispensable that the polymer should be water-soluble or water-dispersible.

As specific examples of the polymer, there can be mentioned an acrylic acid homopolymer, a methacrylic acid homopolymer, an acrylic acid/methacrylic acid copolymer, an acrylic acid/methacrylic acid polyoxyethylene ester copolymer, an acrylic acid/methyl acrylate copolymer, an acrylic acid/vinyl acetate copolymer, an itaconic acid/vinyl acetate copolymer, a saponification product thereof, an acrylic acid/maleic acid copolymer, a maleic acid/isobutylene copolymer, a maleic acid/styrene copolymer, and alkali metal salts, ammonia salts and organic amine salts of these polymers. Two or more of the foregoing polymers can be used.

It is preferred that the amount of the dispersant used in the present invention be such that the weight ratio to the physiologically active substance is from 0.001 to 1, especially from 0.005 to 0.5.

As specific examples of the physiologically active substance used in the present invention, there can be mentioned insecticides such as ethofenprox [melting point=37° C., 2-(4-ethoxyphenyl)-2-methylpropyl 3-phenoxybenzyl ether], Dimethoate [melting point=52° C., dimethyl S-(N-methylcarbamoylmethyl) phosphorothiolthionate], Phosalone [melting point=48° C., S-[(6-chloro-2-oxo-3-benzoxazolyl)methyl]diethyl phosphorothiolthionate) and supracide (melting point of 40° C., S-(5-methoxy-2-oxo-2,3-dihydro-1,3,4-thidiazolyl-3-methyl)dimethyl phosphorothiolthionate], fungicides such as Binapacryl (melting point=66° C., 2-sec-butyl-4,6-dinitrophenyl 3-methylcrotonate) and Fuji-One [trademark] (melting point=54° C., diisopropyl 1,3-dithiolan-2-ylidene-malonate, herbicides such as Phenothiol [melting point=42° C., S-ethyl [4-chloro-o-tolyl)oxy]-thioacetate], Alachlor (melting point=41° C., 2-chloro-2',6'-diethyl-N-methoxymethylacetanilide) and Trifluralin (melting point=49° C., α,α,α-trifluoro-2,6-dinitro-N,N-dipropyl-p-toluidine), and acaricides such as Dimite [melting point=70° C., 1,1-bis(p-chlorophenyl)ethanol].

The physiologically active substance is incorporated in an amount of 10 to 60% by weight in the agricultural chemical composition in the form of an aqueous suspension according to the present invention.

In addition to the above-mentioned indispensable ingredients, an anionic or non-ionic surface active agent can be incorporated in the agricultural chemical composition in the form of an aqueous suspension according to the present invention.

As such a surface active agent, there can be mentioned polyalkylene oxide type non-ionic surface active agents such as polyoxyalkylene alkyl ethers and polyoxyalkylene alkylaryl ethers, and anionic surface active agents such as salts of alkyl sulfates, salts of polyoxyalkylene alkyl sulfates and salts of polyoxyalkylene alkyl phosphates.

The agricultural chemical composition in the form of an aqueous suspension according to the present invention is ordinarily obtained by heating and melting a mixture of a physiologically active substance having a melting point of 15° to 70° C. and a phthalic acid ester and pouring the melt into an aqueous solution containing a dispersant by stirring with a homomixer or the like, and in general, the particle size of the suspended particles is about 5 to about 20μ.

In the agricultural chemical composition in the form of an aqueous suspension according to the present invention, the phthalic acid ester bleeds on the surface of the physiologically active substance to modify the surface, and an emulsion having an excellent storage stability is obtained.

The present invention will now be described in detail with reference to the following examples that by no means limit the scope of the invention.

Phthalic acid esters and physiologically active substances used in the examples are described below.

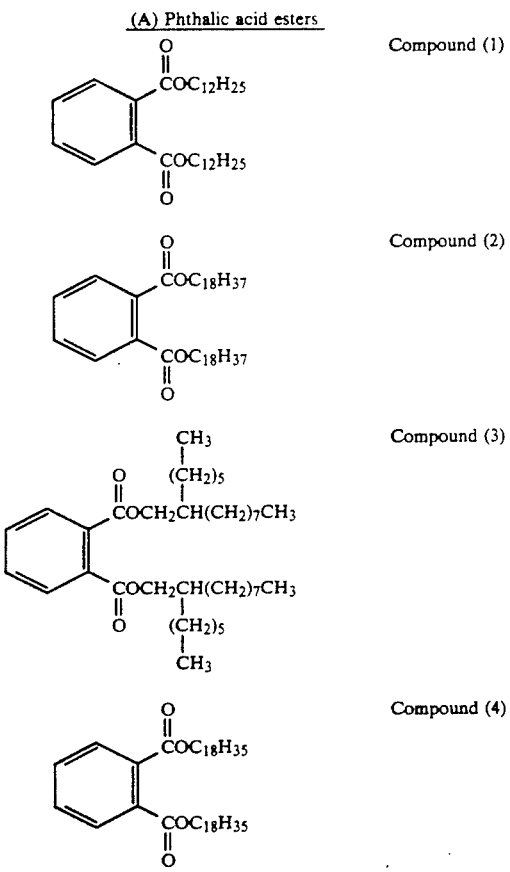

(B) Physiologically Active Substances

Physiologically Active Substance (I)

etofenprox having a melting point of 37° C.

Physiologically Active Substance (II)

alachlor having a melting point of 41° C.

Physiologically Active Substance (III)

trifluralin having a melting point of 49° C.

EXAMPLE 1

A mixture comprising 5 parts by weight of compound (1) and 30 parts by weight of physiologically active substance (I) was molten, and the melt was gradually poured into a solution of 2 parts by weight of a sodium salt of an itaconic acid/vinyl acetate copolymer (molar ratio=1/1) in 63 parts by weight of water by stirring with a homomixer to give a suspension concentrate.

COMPARATIVE EXAMPLE 1

A melt of 30 parts by weight of physiologically active substance (I) was gradually poured into a solution of 2 parts by weight of a sodium salt of an itaconic acid/vinyl acetate copolymer in 68 parts by weight of water by stirring with a homomixer to give a suspension concentrate.

EXAMPLE 2

A mixture comprising 2 parts by weight of compound (2) and 20 parts by weight of physiologically active substance (I) was molten, and the melt was gradually poured into a solution of 2 parts by weight of a sodium salt of a styrene/maleic acid copolymer (molar ratio=1/0.1) in 76 parts by weight of water by stirring with a homomixer to give a suspension concentrate.

EXAMPLE 3

A mixture comprising 10 parts by weight of compound (3) and 30 parts by weight of physiologically active biocidal substance (II) was molten, and the mixture was gradually poured into a solution of 1.0 part by weight of a saponified acrylic acid/vinyl acetate copolymer (molar ratio=1/1) and 0.5 part by weight of sodium polyoxyethylene (5 moles) lauryl sulfate in 58.5 parts by weight of water by stirring with a homomixer to give a suspension concentrate.

EXAMPLE 4

A mixture comprising 15 parts by weight of compound (4) and 30 parts by weight of physiologically active substance (III) was molten, and the melt was gradually poured into a suspension of 1 part by weight of polysodium acrylate in 54 parts by weight of water by stirring with a homomixer to give a suspension concentrate.

COMPARATIVE EXAMPLE 2

A melt of 30 parts by weight of physiologically active substance (III) was gradually poured into a suspension of 1 part by weight of saponified polyvinyl acetate having a saponification degree of 60% in 69 parts by weight of water by stirring with a homomixer to give a suspension concentrate.

COMPARATIVE EXAMPLE 3

A mixture comprising 15 parts by weight of compound (4) and 30 parts by weight of physiologically active substance (III) was molten, and the melt was gradually poured into a solution of 1 part by weight of sodium dodecylbenzene-sulfonate and 2 parts by weight of polyethylene (12 moles) styrenated phenyl ether in 52 parts of water by stirring with a homomixer to give a suspension concentrate.

Test 1 on Stabilization

The suspension concentrates obtained Examples 1 to 4 and Comparative Examples 1 to 3 were each subjected to the storage test where one cycle comprised storing at −10° C. for 3 days and storing at 50° C. for 3 days. After the lapse of a predetermined period, the change of the particle size, the change of the viscosity, the presence or absence of precipitated crystals, the change of the content of the active ingredient and the change of the suspension stability were examine according to the following methods.

The obtained results are shown in Table 1.

Particle size (μ)

The particle size was determined with a coulter counter.

Viscosity (cps)

The viscosity was measured with a Brookfield viscometer (30 rpm at 25° C.).

Precipitated Crystals

The presence or absence of precipitated crystals was checked with an optical microscope (400 magnifications).

Change of Content (%) of Active Ingredient

The content of the active ingredient was determined by gas chromatography.

Suspension Stability (%)

The sample was put in a cylinder having an inner diameter of 2 cm and a height of 10 cm, and the suspension ratio was determined according to the following formula:

$$\text{Suspension ratio (\%)} = \frac{A - B}{A} \times 100$$

wherein A stands for the initial height of the suspension and B stands for the height of the suspension after 20 cycles.

TABLE 1

|  | Particle size (μ) | | Viscosity (cps) | | Absence or presence of precipitated crystals | | Change of content (%) of active ingredient | | Suspension stability (%) | |
| --- | --- | --- | --- | --- | --- | --- | --- | --- | --- | --- |
|  | at start | after 20 cycles | at start | after 20 cycles | at start | after 20 cycles | at start | after 20 cycles | at start | after 20 cycles |
| Ex. 1 | 3.7 | 3.8 | 241 | 260 | absent | absent | 28.0 | 28.0 | 100 | 98.4 |
| Ex. 2 | 3.5 | 3.5 | 290 | 311 | absent | absent | 18.5 | 18.5 | 100 | 99.4 |
| Ex. 3 | 3.0 | 3.0 | 275 | 285 | absent | absent | 28.5 | 28.5 | 100 | 96.5 |
| Ex. 4 | 2.8 | 2.9 | 301 | 300 | absent | absent | 25.0 | 25.0 | 100 | 98.4 |
| Comp. Ex. 1 | 6.9 | 45.0 | 540 | 2400 | absent | present | 28.0 | 22.4 | 100 | 41.0 |
| Comp. Ex. 2 | 10.4 | 85.4 | 555 | 1950 | absent | present | 25.0 | 21.9 | 100 | 42.5 |
| Comp. Ex. 3 | 6.2 | 40.0 | 325 | 74 | absent | present | 30.0 | 39.8 | 100 | 5.4 |

Test 2 to the Herbicidal Effect

The trifluralin suspension obtained in Example 4 and a control emulsion as shown below were each diluted to 300 times and 500 times. Seven ml, per a pot having 12 cm diameter, of each diluted dispersion was sprayed on the 2nd or 3rd leaf stage of crabgrass being 7 cm high, in the number of 30 per a pot. After 14 days, the fresh weight of remaining crabgrass above the ground was measured and a herbicidal extent was obtained in comparison with the non-treated area. Results are shown in Table 2.

The control emulsifiable concentrate comprised 30 parts by weight of trifluralin, 60 parts by weight of xylene and 10 parts by weight of an emulsifier comprising 32 wt. % of calcium dodecylbenzenesulfonate, 48 wt. % of polyoxyethylene(10)nonylphenylether and 20 wt. % of polyoxyethylene(10)sorbitanoleylester.

TABLE 2

| | herbicidal extent (%) | |
|---|---|---|
| | Example 4 | control |
| 300 times | 92 | 86 |
| 500 times | 79 | 70 |

Test 3 to the Insecticidal Effect

Fifth leaf stage of rice plant was planted on a pot having 1/10,000 a and the dispersion obtained in Example 1, having been diluted in the below shown way, was sprayed thereon with a turning table in an amount of 50 ml per 3 pots. After 1, 3, 5 or 8 days, having covered the plant with a cylindrical wire net, 10 male adults of green rice leafhoppers and 10 male adults of small brown planthoppers were set free inside each covered pot. After 24 hours, the killed insects were counted and an insecticidal extent was obtained on the average about 3 pots. Results are shown in Table 3.

The control emulsifiable concentrate was tested in the above shown way, comprising 21.5 parts by weight of the physiologically active substance (I), 6 parts by weight of Solpol 355TLL (trademark) being available from Toho Chemical Co., Ltd., a mixture of 60 parts by weight of polyoxyethylenestylylphenylether and 40 parts by weight of calcium alkylarylsulfonate and 83.5 parts by weight of xylene.

TABLE 3

| | | insecticidal extent (%) | | | | | |
|---|---|---|---|---|---|---|---|
| | | green rice leafhopper | | | small brown planthopper | | |
| dispersion | content (ppm) | 1 day | 5 days | 8 days | 1 day | 3 days | 5 days |
| Example 1 | 25 | 100 | 97 | 87 | 100 | 85 | 67 |
| | 50 | 100 | 100 | 97 | 100 | 95 | 83 |
| | 100 | 100 | 100 | 100 | 100 | 100 | 93 |
| control | 50 | 100 | 100 | 40 | 87 | 35 | 10 |
| | 100 | 100 | 100 | 67 | 100 | 67 | 17 |

It is noted in the results that the agricultural chemical composition of the present invention is superior to the control in the insecticidal effect.

Test 4 to the Insecticidal Effect

Sample A was obtained in the same manner as shown in Example 1 and treated in the same way as shown in Test 1. Separately Sample B was produced in the same manner as shown in Example 1, not being treated in Test 1. Both Samples A and B were tested in the same way as shown in Test 3. Results are shown in Table 4.

TABLE 4

| | | insecticidal extent (%) | | | |
|---|---|---|---|---|---|
| | | green rice leafhopper | | small brown planthopper | |
| Sample | content (ppm) | 1 day | 5 days | 1 day | 5 days |
| A | 50 | 100 | 100 | 100 | 80 |
| | 100 | 100 | 100 | 100 | 87 |
| B | 50 | 100 | 100 | 100 | 83 |
| | 100 | 100 | 100 | 100 | 93 |

It is noted in the results that the agricultural chemical composition of the present invention continues providing its biological effect even after it has been left for some period of time for storage.

I claim:

1. An aqueous biocide composition which comprises 10 to 60 wt. % of a water-insoluble, physiologically active substance, said substance being in the form of fine particles and having a melting point of 15° to 70° C., 0.001 to 10 wt. % of a water-soluble or water-dispersible polymer, said polymer comprising one or more monomer units selected from the group consisting of unsaturated carboxylic acids and derivatives thereof, 0.01 to 30 wt. % of a phthalate, and the balance being water.

2. A composition as claimed in claim 1, which comprises 10 to 60 wt. % of the physiologically active substance, 0.01 to 10 wt. % of the polymer, 0.1 to 30 wt. % of the phthalate and the balance of water.

3. A composition as claimed in claim 1, in which the physiologically active substance is selected from the group consisting of insecticides, fungicides, herbicides and acaricides.

4. A composition as claimed in claim 1, in which the unsaturated carboxylic acid or its derivative is selected from the group consisting of acrylic acid, methacrylic acid, maleic acid, itaconic acid, an alkyl ester of the acid, an alkali metal salt of the acid, an ammonium salt of the acid and an organic amine salt of the acid.

5. A composition as claimed in claim 1, in which the polymer is a copolymer with vinyl acetate, isobutylene, di-isobutylene, an alkylene ether or styrene.

6. A composition as claimed in claim 1, in which the phthalate is a mono-ester or di-ester of phthalic acid and an alcohol having 4 to 22 carbon atoms.

7. A composition as claimed in any of claim 1, which further comprises up to 20 wt. % of a nonionic or anionic surfactant.

8. A composition as claimed in any of claim 2, which further comprises up to 20 wt. % of a nonionic or anionic surfactant.

9. A composition as claimed in claim 6, in which the phthalate is a di-ester.

10. A composition as claimed in claim 6, in which the alcohol has from 10 to 18 carbon atoms.

11. A composition as claimed in claim 8, in which the phthalate is a di-ester of phthalic acid and the alcohol has from 10 to 18 carbon atoms.

12. A composition as claimed in claim 1, in which said substance is 2-(4-ethoxyohenyl)-2-methylpropyl-3-phenoxybenzyl ether, said polymer is a sodium salt of an itaconic acid/vinyl acetate copolymer and said phthalate is didodecyl phthalate.

* * * * *

UNITED STATES PATENT AND TRADEMARK OFFICE
CERTIFICATE OF CORRECTION

PATENT NO. : 5 090 995
DATED : February 25, 1992
INVENTOR(S) : Yutaka KUBOTA et al It is certified that error appears in the above-identified patent and that said Letters Patent is hereby corrected as shown below:

Column 8, line 50; delete "any of".
          line 53; delete "any of".

Signed and Sealed this

Twentieth Day of July, 1993

Attest:

MICHAEL K. KIRK

Attesting Officer      Acting Commissioner of Patents and Trademarks